United States Patent [19]

Snook

[11] Patent Number: 5,110,200
[45] Date of Patent: May 5, 1992

[54] VIDEO KERATOMETER

[75] Inventor: Richard Snook, Houston, Tex.

[73] Assignee: Technitex, Inc., Houston, Tex.

[21] Appl. No.: 374,425

[22] Filed: Jun. 30, 1989

[51] Int. Cl.$^5$ .............................................. A61B 3/10
[52] U.S. Cl. ..................................... 351/212; 351/221
[58] Field of Search ................ 351/206, 214, 212, 221

[56] References Cited

U.S. PATENT DOCUMENTS

| Re. 27,475 | 9/1972 | Volk ...................................... 351/39 |
| 3,248,162 | 4/1966 | Knoll ...................................... 351/6 |
| 3,264,932 | 8/1966 | Hendricks ............................... 88/24 |
| 3,542,458 | 11/1970 | Volk ...................................... 351/39 |
| 3,598,478 | 8/1971 | Towneley ............................... 351/6 |
| 3,797,921 | 3/1974 | Kilmer et al. .......................... 351/7 |
| 4,439,023 | 3/1984 | Iba et al. ............................... 351/206 |
| 4,440,477 | 4/1984 | Schacher ............................... 351/212 |
| 4,523,820 | 6/1985 | Kaakinen .............................. 351/206 |
| 4,523,821 | 6/1985 | Lang et al. ............................. 351/214 |
| 4,863,260 | 9/1989 | Gersten et al. ........................ 351/212 |

OTHER PUBLICATIONS

"Holographic process offers best potential for real-time modeling" *Ocular Surgery News*, Feb. 15, 1988, vol. 6, No. 4.
W. A. Douthwaite, "A New Keratometer", *American Journal of Optometry & Physiological Optics*, vol. 64, No. 9 (1987), pp. 711-715.
Leo J. Maguire, et al., "Graphic Presentation of Computer Analyzed Keratoscope Photographs", *Tech Ophthalmol*, vol. 105, Feb. 1987, pp. 223-230.
Geo. W. Tate, Jr. et al., "Accuracy and Reproducibility of Keratometer Reading" *CIAO Journal*, vol. 13, No. 1, Jan. 1987.
Thomas Olsen, "On the calculation of power from curvature of the cornea," 70 *British Journal of Ophthalmology* 152-154, 1986.
James Rowsey, et al., "Corneoscopy in Keratorefractive Surgery," 2 *Cornea* 133-142, 1983.
James D. Doss, "Method for Calculation of Corneal Profile and Power Distribution," Arch Ophthalmol, vol. 99, Jul., 1981, pp. 1261-1265.
Sami G. El Hage, "A new conception of the corneal topology and its application" *Optica Acta*, vol. 19, No. 5, 1972, 431-433.
Sami G. El Hage, "Nycthemeral Rhythm of the Cornea and Night Myopia," *American Journal of Optometry and Archives of American Academy of Optometry*, Dec. 1971.
Richard F. Brubaker, "Meridional Refractometry," *Arc Ophthal*, vol. 81 Jun. 1969.

Primary Examiner—Paul M. Dzierzynski
Attorney, Agent, or Firm—Michael F. Heim

[57] ABSTRACT

A Keratometer for ascertaining the shape of the corneal surface of the eye comprises a television camera with associated processing circuitry. The television camera receives a reflection of a target such as placido's disc from the surface of the cornea. The television image of the reflection of the placido disc from the corneal surface is subjected to digital analysis after treatment in an edge detector. The edge detector reduces the number of data points that must be processed to define the radius of each ring in the reflected placido disc image. The resultant data are processed to derive surface contour and to provide a display in tabular, graphic or pictorial form of the contour data so generated.

9 Claims, 7 Drawing Sheets

VIDEO KERATOMETER

BACKGROUND OF THE INVENTION

The present invention relates to improvements in the art of photo-keratometry and more particularly to the use of television techniques to ascertain the contour of the cornea. A keratometer is an instrument for determining the shape of the corneal surface which generally uses a placido or other illuminated target that is viewed by the patient. The reflection of a placido or other target by the tear film on the anterior surface of the cornea is analyzed to determine the surface contour of the eye.

The technique in modern form dates from the early thirties when the Zeiss optical company of Germany introduced a "Photo Keratoscope". In general, the art has required the image reflected by the eye to be photographed and the image on the film measured in a second step to derive the data from which the contour map is generated.

Recent improvements have been in the area of automating this photogrammetric analysis by re-imaging the photograph with television apparatus and digital signal conversion. After digitization, computer analysis of the resultant information is performed with conventional image analysis algorithms. This type of data analysis is computer intensive and the image formed by the television system contains a large amount of redundant and extraneous information. For adequate resolution the sampling rate must exceed the data frequency by at least three to one, thus generating a huge number of data points for mathematical analysis. Consequently the systems are costly, complex, slow and often lack real resolution in the image analysis.

Other means have been used for clinical measurements such as direct casting of the eye surface in plastic or wax and coating the cornea with talcum powder and projecting a grid on this surface for photogrammetric analysis. At present, the clinical standard is the Bausch and Lomb Keratometer, which is sold commercially. The Bausch and Lomb Keratometer only measures the average of the corneal radius in two meridians of the central 3 mm "cap" of the cornea. The standard technology does not provide total surface topography of the cornea and thus is inadequate for many diagnostically significant abnormalities or the needs of some surgical procedures. In addition, the prior art technique is cumbersome and involves great potential for error.

The initial development in keratometry came from Gullstrand in 1896. Gullstrand disclosed the foundation for the current technology but his apparatus had no provision to compensate for aberrations in the optical system other than limiting the photographic coverage of the cornea to a 4 mm area. As a result, multiple exposures and calculations were necessary to map the corneal surface.

Much of the modern technique was developed by Amsler in 1930 and embodied in his "Photo-Keratoscope" which also required measurement and calculation as a separate step to derive the corneal shape data.

As noted supra, the standard instrument which is in most common use for central optical zone shape measurement is the Bausch and Lomb Keratometer. Several companies offer similar devices with similar principles of operation. In these devices two perpendicular axes are used to create an image of a small portion of the anterior surface of the cornea. The user is required to operate several controls to bring Mire images reflected from the two perpendicular axes simultaneously into focus and alignment. In addition, the operator manually records the data obtained. Other instruments are also available, such as the Haag-Streit Javal Schiotz device which measures only one axis at a time, but is slightly easier to use and tends to be more accurate in practice than the Bausch and Lomb system. In addition there exists a photo system made by International Diagnostic Instrument Limited under the trademark "CORNEASCOPE" (and a similar system made by Nidek in Japan), as well as autokeratometers by several manufacturers. The CORNEASCOPE produces Polaroid photographs of the reflection of a placido disc and requires a second instrument separate from the camera assembly to analyze the data. This system is fairly accurate, but expensive and tedious to use. The autokeratometers all are limited to a single zone of approximately 3 mm diameter and, in cases where the magnitude of the astigmatism is low, are inaccurate in their assessment of axes of astigmatism. Also available are three computer-direct systems which use conventional image analysis algorithms in conjunction with a mini-computer. These are the previously mentioned Computed Anatomy system, the ECT-100, recently introduced into the market by Optimed of Alphareta, Ga., and a system using light emitting diodes disposed in concentric rings built by Zeiss of Germany. The placido disc-photo technique is superior to the Bausch and Lomb Keratometer because of the much greater amount of information about zonal shape which may be obtained from the placido reflex as opposed to the mires of the Keratometer.

A number of patents have been issued that relate to keratometers. U.S. Pat. No. 3,797,921 discloses the use of a camera to record the placido reflex from a patients eye. From this photograph, the radius of surface curvature of the cornea is determined at several points and calculated using a complex computer system. The use of a ground glass focusing screen with the small aperture of the optical system and large linear magnification makes use difficult and requires a darkened room for operation.

U.S. Pat. No. 4,440,477 discloses a method and device for measuring the corneal surface, comprising a slit lamp for illuminating the corneal surface, a camera for recording the reflection from the corneal surface, and a processor to calculate the image distance and the radius of curvature of the eye. The operation of the processor is not detailed in U.S. Pat. No. 4,440,477.

A more recent entry into the market is the "Corneal Modeling System" manufactured by Computed Anatomy Incorporated of New York which uses a scanning laser in conjunction with a "frame grabber" to digitize and store for conventional image analysis the pictorial data. The placido is in cylindrical form which requires large depth of focus of the imaging system and, consequently, sophisticated focus determining apparatus to assure accurate image evaluation. This system is said to produce corneal thickness data as well as the surface contour but is very expensive and does not lend itself to clinical applications which are increasingly cost driven.

All the prior art systems are both expensive and difficult to use. The prior art devices all have a significant potential for error, due to complexity of the calculation, the imaging of the corneal surface and the difficulty in operating these systems. The traditional approach to photo-keratometry has been very software intensive and thus quite costly. In addition, the digitized image occupies a large portion of memory. The digitized image must occupy only a portion of the available memory in any computer system if there is to be the capacity to act upon the image information. For example, if the image is composed of some 400 active lines, each line must be subdivided into elements for storage. If equal horizontal and vertical resolution are required, then 533 elements must be converted and stored for each video line (given the standard 4:3 aspect ratio). This would result in 213,000 elements to be stored (400×533). In addition, the program, which involves complex computations, would use a large amount of memory for program and variable storage. From this it follows that some other system must be employed to produce a functional instrument within clinical cost constraints and operable by unsophisticated users. These and other criteria require that a departure from the traditional techniques for Keratometry and image analysis be employed.

SUMMARY OF THE INVENTION

Accordingly, there is provided herein a new technique for video image analysis that provides full topographical mapping of the cornea, with almost instant display of the corneal radius of curvature at enough points to permit accurate assessment of the surface shape. The improved photo keratometer includes, a transilluminated target or "placido", which is reflected by the surface of the eye to be examined. A television camera and lens system is mounted behind the placido so that the optical axis is coincident with the axis of the eye being examined and is generally centered in the target member to provide an image of the reflection of the target by the eye. The image information from the television camera is then treated in edge detection circuitry to derive the locus of image brightness discontinuities which are associated with the target reflection from the eye. These image points are, in turn, transferred to storage in the internal memory as digital representations of the x, y locus of the image brightness discontinuities.

The stored data associated with the television image of the target reflection are then treated in a conventional electronic computer to derive the surface contour of the eye and to generate the display of the derived shape information for use by the operator. The videokeratograph described herein can serve as a sensitive method to determine proper contact lens fit by measuring the shape of both surfaces of the contact lenses and comparing these shape measurements with the shape of the eye to which the said lens is to be applied.

DETAILED DESCRIPTION OF THE INVENTION:

I. System Overview

The present invention requires a rudimentary knowledge of optics and television signals. A television image which seems to the viewer to be a single stable image is in fact a blank screen most of the time. The human visual system is tricked into the perception of a whole picture by making use of the persistence of vision and other psycho-physiological phenomena. The picture is "drawn" by a beam of electrons which strike a phosphor coating inside the faceplate, or viewing surface, of the cathode ray tube where the image is formed. The phosphor emits visible light in direct proportion to the number of electrons per unit time which strike it and the energy of the particles in the beam. The beam is formed by thermal emission and electrostatic acceleration in an "electron gun" within the neck of the tube, behind the viewing surface and thus out of view. The beam is focused by an electrostatic lens within the gun assembly so that the area bombarded at any instant is quite small compared to the entire screen. The illuminated spot is on the order of a few thousandths of an inch in diameter. This area is the only area on the entire screen which emits light to any significant extent at any given instant. The beam is swept over the surface of the faceplate in a regular pattern called a "raster". The raster is generated by deflecting the beam of electrons by an electromagnet assembly called a "yoke". The beam is driven to the upper left corner (as viewed) at the start of each picture interval. It then sweeps across the faceplate from left to right to the other edge of the screen. At that time, the beam is turned off or "blanked" for a short time while the yoke signal is changed to start a new line at the left edge of the screen slightly below the first line. After this "retrace interval", the beam is "unblanked" and the process is repeated.

In the U.S. domestic NTSC standard, the actual image or "frame" is made in two interdigitated or "interlaced fields", each of which is made up of 262.5 such lines (some of these lines do not result in any image formation but are outside the viewing area). As the raster is drawn, the intensity of the beam is modulated by the incoming signal so that the intensity of the light produced per unit area is a faithful reproduction of the transmitted scene. The image can be thought of as a large number of discrete areas or picture elements ("pixels") which are painted on the screen in time sequence. The pixel, the smallest discrete pictorial element, is limited by the information transfer rate available. This rate was set for commercial broadcasting to fit in the amount of radio spectrum available. The transmitted signal contains the synchronizing information required to keep the locus of the beam at any time in step with the source to insure undistorted restructuring of the data into a picture. These "sync" signals are included in the transmission as a part of the horizontal and vertical blanking intervals. The line rate and the pixel rate define the size of a pixel in terms of pixels per line or pixels per second. In conventional broadcast television the signal is limited to 4.5 Megahertz, which yields a pixel rate of only 236 for the active or visible line of some 52.4 microseconds even though the overscan of the display means that even fewer pixels make up the actual image viewed by the user. These facts limit the inherent resolution of a broadcast television picture to a level much less than even a poor photograph, but the apparent motion and several other factors cause the perceived image to be acceptable when used as an entertainment medium. A computer generated display is structured in similar fashion to make use of components which are in volume production. Some of these systems use a much higher line and pixel rate to obtain the resolution needed for computer aided design applications, up to 2000 pixels per line on a 1000 line raster for example, but they are very expensive and complex and thus not viable for use in a system which is cost driven. This invention can make use of common industrial surveillance-type camera and monitor apparatus without extensive modification. It should be noted that use of a combination of European PAL (Phase Alternate Line) and domestic standards may be employed to provide 625 lines per frame with a field rate of 60 per second without difficulty to bring the horizontal and vertical resolution more nearly into balance. For example, the picture can be made up of 625 lines as in the european format but at the faster 60 fields per second of the NTSC format. This modification is simple to make on cameras or monitors but requires that both be modified for use. To take complete advantage of this resolution enhancement the data contained in both sequential fields is required. Because the cornea of the eye is essentially circular in form, the normal television picture aspect ratio of 4:3 provides no advantage. If the camera and monitor are modified as stated above and 750 pixels per line are generated, the size of a pixel can be made equal in height and width without much increase in data bandwidth. This technique can then provide a frame resolution of 625×625 pixels for the central square area without exotic modification of either camera or monitor. The generation of square pixels by this or some other method reduces the complexity of the computational steps required to define the corneal shape without material increase of cost or complexity.

The optical portions of this invention are not very complex and a few simple equations and diagrams will serve to illustrate the principles to be employed.

Figure 9:
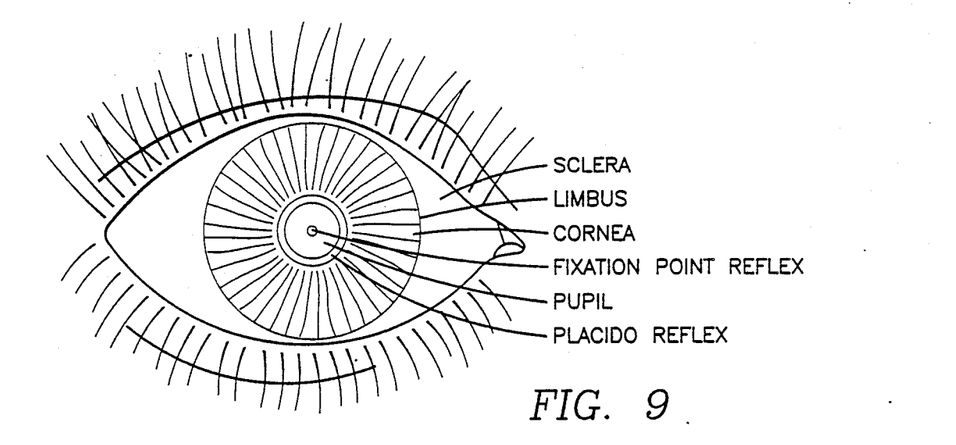
FIG. 9 shows a front view of an eye with a placido reflection.
Figure 10:
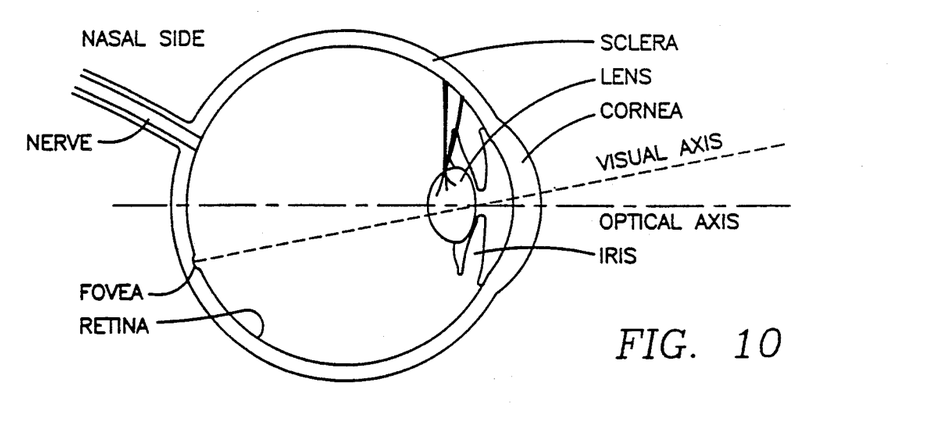
FIG. 10 illustrates a horizontal cross-sectional view of an eye.

FIGS. 9 and 10 illustrate the more important features of the eye as they relate to keratometry. The pupil of the eye is defined by the central area surrounded by the iris. The iris opening size is controlled by the autonomic nerve system in relation to the brightness of illumination as well as other factors and may be as small as one millimeter in diameter to five millimeters in diameter in dim light. The constriction of the iris in bright light also provides an increase in depth of focus such as is observed in conventional photography. The reflection of the one or more concentric rings of the placido will appear as more or less circular bright rings superimposed on the iris when viewed by the television camera. The interior of the eye is shown as a horizontal cross-section to show the more important structures. The globe is enclosed in a semi-rigid white membrane called the sclera. The transparent membrane at the front is called the cornea. The cornea is a thin membrane which is supported in shape by the pressure of the fluid behind the membrane and in front of the crystalline lens. The lens is supported by a system of filaments and muscle tissue which cooperate to change the thickness and, in consequence, the focal length of the lens. The primary focusing power of the optical system of the eye is the action of the cornea and the fluid filling the anterior chamber, while the lens serves to permit the change of plane of focus from near objects to distant scenes. The light entering the eye through the iris opening is brought to focus on the surface of the retina which lines a large portion of the globe and contains the photoreceptor cells. These cells are of two general types, rods and cones. The rods predominate in the areas peripheral to central image and are highly sensitive to light but devoid of color sensitivity. The rods provide "scotopic" or night vision. The cones predominate in the central retina and in the "fovea", where critical central vision takes place there are no rods at all. The center of vision is located in the fovea which is displaced from the optical axis of the eye by some five to seven degrees. Because the surface of the cornea is not a perfect spherical section the curvature of the surface is asymmetrical around the center of vision and must be taken into consideration in keratometry.

As noted in U.S. Pat. Nos. 3,542,458 and 4,440,477 the reflection of an object in a convex mirror will produce an image which is "virtual" (cannot be formed on a screen, but can be viewed directly) erect, and reduced in size by an amount which is a function of the radius of curvature of the mirror. In this system, the tear film and/or the surface of the cornea acts as such a mirror. The formula often used to define the light reflected from a transparent surface is:

$$x = (n_1 - n_2)^2/(n_1 + n_2)^2$$

where the values of n are the indexes of refraction of the two media of transmission. air to tear film and tear film to cornea. The values of 1.000 for air, 1.333 for the tear film and 1.337 for the cornea are commonly used. This would imply that there is approximately a two percent reflection at both the optical interfaces, i.e. the tear film and anterior corneal surface. The small thickness of the tear film places both reflections in close proximity so that they are indistinguishable from each other for instrumental purposes. As a result these reflections are lumped together for clinical applications. However, the small amount of light in the reflected pattern influences the system design, as will be discussed infra.

The anterior surface of the normal cornea is not quite spherical, as is assumed in the construction of many of the prior art devices such as the Bausch and Lomb Keratometer, but is more nearly an evolute ellipsoid. The central two or three millimeters of the normal cornea does conform reasonably to the spherical form so the simplistic model will serve to illustrate the optics of the system for rays at or near the common optical axis.

To select the camera and lens which form a part of the present invention, some compromise is required. The larger tubes provide better resolution but cost more. One standard camera tube is two-thirds inch (approx. 18 millimeters) in diameter. The desired image is on the order of eleven millimeters in diameter or somewhat less, to permit all of the placido reflection to be seen in every instance. For purposes of this invention it is assumed that the diameter is equal to the diagonal of the image formed on the active surface of the camera tube. The image sizes for the other common tubes are, 16 mm for the one inch tube and 8 mm for the one half inch type. The size of the image is chosen to meet the previous limitation so that the outer reflection will be visible in the television picture with a minimum of extra coverage. This means that the image of the placido reflection preferably will be on the order of ten millimeters in diameter. In the case of a system with square pixels, the geometry changes slightly, but this example of the normal 4:3 aspect ratio illustrates the general principles employed. From this the camera and objective lens distance from both the eye and the tube may be calculated. With the magnification ratio known, the effective aperture can be determined. This permits the estimation of the faceplate illumination to be available for any given placido illumination level. The illumination level is a compromise between discomfort of, or hazard to, the subject and signal to noise ratio for the system. Quite low levels are practical as compared to the photographic technique used in the prior art.

As the angle of the reflection relative to the optical axis increases, object size must increase for a fixed object plane to image plane distance. To compensate for optical aberration induced error of calculated curvature of the cornea, a table is used to compensate for the amount of curvature of the cornea. It follows that the table value must be a compromise in that the image must subtend a finite width to be visible and, consequently, the various portions of the image are displaced by slightly different amounts. The table values are derived from measurements made from spherical objects of known diameter. The derived data are in the form of spherical equivalent curvature at the various distances from the assumed optical center and as such are not strictly a true surface shape. The amount of error thus introduced is not of any significance for clinical use of the instrument. A similar method has been used by U.S. Pat. No. 3,797,921, incorporated by reference number, but the hemispherical form of the placido in U.S. Pat. No. 3,797,921 makes interpolation difficult because the table is nonlinear in both directions.

The actual measurement of the image preferably is done by subdividing the image line into small elements of time, which are examined for brightness information. A yes/no decision is made from these bits of data for each pixel. There is a definable relationship between the pixel and the size of the image on the camera tube faceplate and hence the object. In the system disclosed in the present invention, the "clock" signal is derived from a highly accurate crystal controlled oscillator. In the preferred embodiment of the invention, the crystal oscillator operates at 14,318,180 cycles per second. This frequency is chosen to permit false color overlay generation of the data points on the camera image for operator convenience and is an integral multiple of the color sub-carrier frequency used by NTSC (National Television System Committee, the U.S. standard for television broadcasting) color systems and is commonly available from PC type computers. Any selected clock frequency must be made phase coherent with the horizontal sync so that the horizontal locus of each pixel will be constant. The horizontal line is thus divided into pixels with a definable size in terms of placido image which, in turn, relates to the radius of curvature of the eye surface at the point where the image radius is defined. A pixel rate of approximately 14,300,000 per second divided by the frame rate yields 238,600 pixels per image, each of which can have one of many brightness levels. The active line time divided by the reciprocal of the clock rate gives a numerical solution of 750, which is to say that the yes/no decision relating to image brightness is made 750 times on each line or that there are 750 pixels per line. This compares with the previously described NTSC resolution of 235, or the 525 elements available in solid-state cameras such as are employed by one of the extant systems.

With, for example, an outer placido ring of 165 mm and an inner ring of 55 mm with a 75 mm object to eye distance, the values listed below indicate some of the values which might be presented to the camera system for analysis:

| Corneal radius | Corneal surface curvature: | |
|---|---|---|
| | Inner ring image size | |
| (in mm) | (in mm) | (in pixels) |
| 7.70 | 3.662 | 262 |
| 7.79 | 3.702 | 264 |
| 7.80 | 3.707 | 265 |
| 7.90 | 3.752 | 268 |
| 8.00 | 3.797 | 271 |

The user is most often interested in data presentation in terms of diopters of focusing power of the cornea and the radius information can then be converted to this form as follows:

$$d = (n-1)/r$$

where the index of refraction of the cornea, n, is assumed to be 1.3375 and the radius of curvature of the corneal surface, r, is expressed in meters. It should be noted that there is not an agreement on the actual value of the effective index of refraction to be employed in placidos method of keratometry and that the calculation of corneal curvature in dioptric form also involves optical correction factors to compensate for the effectively negative "lens" formed by the rear surface of the cornea. In practice the value of index of refraction used by several systems for this conversion range from 1.332 (Zeiss) 1.336 (American Optical) to 1.3375 (Haag-Streit and Bausch & Lomb). The "normal" range of curvature in the central zone ranges from 7.2 to 8.3 mm with a mean value of 7.8 mm. Some representative values for the Bausch & Lomb instruments converting the readings into diopters are shown in the following table:

| Dioptral curvature | surface radius in mm |
|---|---|
| 61.0 | 5.53 |
| 60.0 | 5.63 |
| 47.0 | 7.18 |
| 45.0 | 7.5 |
| 44.0 | 7.67 |
| 42.0 | 8.04 |
| 41.0 | 8.23 |

From the foregoing it follows that the conversion of the data into dioptric form is trivial and involves the use of a selected constant but that the data so expressed is subject to variable error inherent in the technique. The common keratometer has been used for many years with data in dioptric form, even though the magnitudes are not precisely accurate. The choice of display form is selectable in this invention to permit the user to choose between the more accurate and the more common form. The display of the derived data may be in graph form for ease of assimilation and application by the user. This is by using conventional display algorithms and techniques which are machine dependent and will not be discussed in detail herein.

The data of interest to the user are the radii of the chord of the placido reflex in any of the possible directions and the dioptral curvature of the surface at each of these points. The keratometer of common use measures two perpendicular meridians at each selected angle and produces data in the form of "K1, K2", Cylinder and axis. These terms refer to the average dioptric curvature in the two axes which have the greatest and least curvature, assumed to be 90 degrees apart in "regular" astigmatism, the magnitude of the difference between the two, and the angle relative to the horizontal of the larger of the two. The terms are commonly used and are recognized by the user as definitive of these descriptive elements as derived by conventional keratometry. The axis can either be measured or assumed to be regular (90 degrees apart), which is probably acceptable for most measurements. In the event that the user desires more accurate data in respect to axis, the entire measuring portion of the instrument is rotated around the optical axis and a more accurate derivation of the two (major and minor) K values is obtained by a process of repeated measurement and recordation.

To reduce the amount of data required to define the ring image size in radial terms, only those pixel loci which define a change of brightness greater than a threshold value are stored. Each ring reflection produces one data point at each reflection edge. These points can be used to determine the actual locus of the center of the ring reflections. The optical system is preferably provided with an optical fiber which defines the optical center of the system and provides a bright point of light for the patient to fixate upon. The reflection of this small point from the cornea provides a true center from which all measurements are made. Further the numerical scatter of the data points is a function of the focus and overall image quality which permits the evaluation of each measurement for minimum acceptable quality. The decision to reject any measurement which does not fulfill the quality standard is set into the software. This is due to the requirement that the object distance be known and fixed for accurate data analysis. Small errors in focus can degrade the measurement and so an optical system with small depth of focus and a software scatter determination are used to insure accuracy. The central fixation target reflection from the optical fiber is also examined for relationship to the true center of the picture and if the image is decentered in either axis by a predetermined amount the measurement is invalidated. The shadow cast by the nose, brow, lashes, etc. as well as the lid margin which may lie within the camera field will cause some data points to be missing from the theoretical maximum number. The lash shadows will not completely obscure the area to be measured and so some minimum number of valid points may be selected which will permit the areas thus partially masked to be defined with a large degree of confidence. The entire picture is examined for brightness transitions in this manner and the axis determined by mathematical algorithms in the computer. Given that, for example, the image resolution of the system provides a pixel size, placido image referred, of 0.014 mm (750 pixels = 10 mm so one pixel = 1/75 mm or 0.0133 mm) then an estimate of the minimum curvature difference and radial interval detectable by the system can be derived.

For best accuracy, each instrument must be calibrated after assembly to compensate for minor differences in system magnification and linearity to obtain maximum accuracy of the derived data. For this reason calibration means preferably are provided as a part of the computer software and the user may check the calibration and reset the table values at any time.

Figure 4:
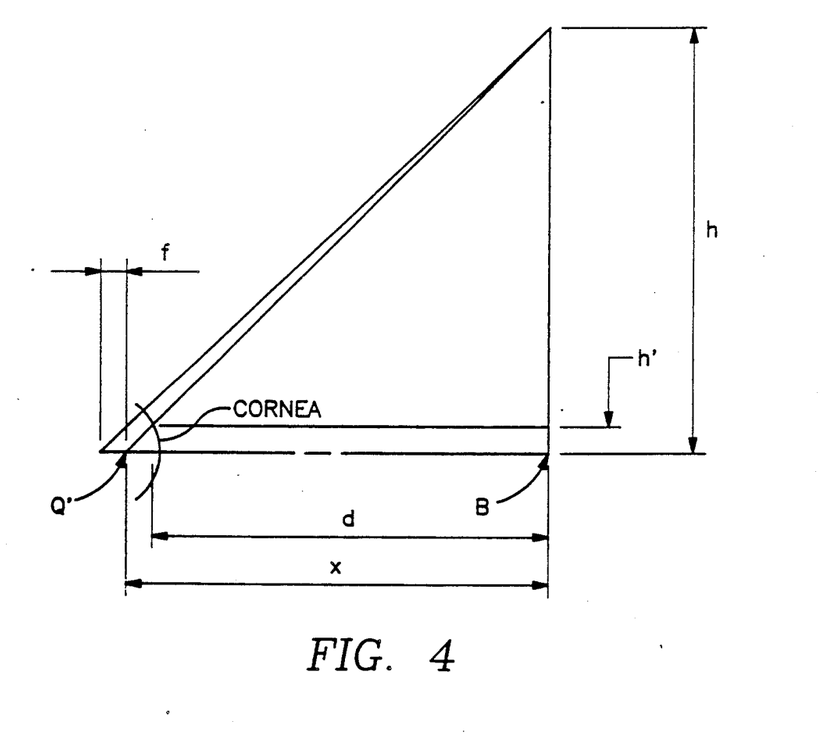
FIG. 4 illustrates an optical theory diagram.

Referring now to FIG. 4. The optical theory diagram shows some of the relationships which are of interest in the present invention.

An object (the cornea of the eye to be measured) with a size h is imaged by reflection at plane d with an image size h'. The magnification is derived by the usual formulae:

$$m = h'/h$$

The focal length of a convex mirror is negative and equal to one-half of the radius of curvature. The sum of the reciprocals of the object and image distances is equal to the reciprocal of the focal length. These two can then be combined to the form:

$$1/o + 1/i = 1/-f = -2/r$$

or $$i = or/[2(or) - r]$$

It follows that the remainder of the image is formed in a similar fashion and that the same figure applies in any meridian. (These formulae are only true for rays which are very close to the optical axis). From the size of object, size of the image, the distance and the optical magnification, the radius of curvature can be calculated as follows:

$$R = M(2U/O)I$$

Where:
 M is the magnification constant of camera and optics;
 U is the distance from object to cornea;
 I is the observed size of image; and
 O is the actual size of object.

The objects imaged are the several rings of the target which yield the curvature of the eye at several distances from the center of the cornea. For the $i^{th}$ ring, all the constants are lumped into one, $K_i$, thus:

$$R_i = K_i I_i$$

$R_i$ is the radius of curvature of cornea of the ith ring;
$I_i$ is the observed size of ith ring; and
$K_i$ is the ith ring conversion constants.

Thus, all that is needed for computation of curvatures, are the $K_i$ constants. The $K_i$'s can be calculated but it is much easier, and more accurate, to measure them by calibrating the instrument with balls of known, precise diameter $R_o$ and setting all $K_i = 1$. The values of $V_i$ are measured which provides a measurement of $I_i$ since $V_i = 1 \times I_i$. Thus, the constants are determined by:

$$K_i = R_o/V_i$$

Where:
 $R_o$ is the known radius of calibration ball; and
 $V_i$ is the measured radius of calibration ball with $K_i$ set to 1.

According to conventional techniques a table is constructed to provide a lookup system for conversion of measured reflex diameters, representing a range of known surface curvature values. In this manner the necessary degree of precision may be achieved to assure accurate output data accuracy for the intended application. Extrapolation between table entries is quite practical and reduces the number of table entries needed to assure accurate measurements. The shape of the placido will determine the nature of the table interpolation which is simplest with the planar form of the placido.

A more exact surface shape characterization could, in theory, be obtained by the method iterated by Wittenberg and Ludlam in a paper published in the Journal of the Optical Society of America Vol. 56 No. 11, November 1966 but the simpler form provides adequate accuracy for clinical use. The magnification factor and the effective numerical aperture are chosen as a compromise between the most desirable small relative aperture and acceptably small depth of field to facilitate the setup and focusing step. This provides an acceptable error from subject positioning resulting from inability to judge small differences in subject distance due to the depth of focus of the optical system as well as adequate image brightness for noise reduction. In most, if not all cases, the exact surface contour is of less interest to the clinician than the relative contour. For example, in a surgical application, the object is to arrive at a smooth, regular corneal surface, which has a similar shape in two perpendicular axes. That is to say that the corneal astigmatism is minimal. The errors of measurement are least at, or near, the center of the cornea and the main image forming surface is encompassed by the same area. Therefore small error accumulation in the periphery of the cornea are tolerable. In surgical procedures where the cornea is cut suture tension and location can alter the surface shape. The peripheral curvature must be maintained as closely as possible to the same value in all axes if there is to be no induced post-operative astigmatism. The keratometer can provide information for post-operative adjustment of sutures to better achieve this result. The shape derivation for contact lens fitting is also a comparative process in that the lenses may also be measured by the instrument and so small errors from true surface derivation cancel and the resulting data are usable in a clinical context.

Because the eye is centered in the picture by adjustment of the instrument and headrest at the time of setup and because the subject is fixating on a target which is coaxial with the system's optical axis, the center of the reflected image and thus, the cornea can be located exactly by a rather simple software technique. The largest difference between the two central image points from the fixation lamp reflection constitutes a measurement that is equivalent to a diameter of the placido reflection (in pixel terms). One-half of that measured value is the center of the figure. The remainder of the analysis is based upon similar technique and is much less software intensive than the classical image analysis algorithms which make more complex decisions about a much larger number of pictorial elements each of which may have one of many numerical values which may represent intensity, saturation and hue. Thus it can be seen that this system substitutes novel means and method for the conventional image analysis technique to permit the construction of a very inexpensive system which can be used to produce clinically useful data when operated by unsophisticated users within the economic constraints imposed by clinical fee structures.

The computer program controls measurements, data analysis and display format. Each single measurement consists of measuring the edges of the placido reflection in view. Subsequent to the data gathering step, the curvatures are computed from the available edges. Any values falling outside of a window of selectable size are considered "bad". Then the half chord measurements for each ring from the selected data points are derived. The values of curvature are similarly computed for each ring image on each side of center at enough angles to permit accurate assessment of major and minor axis angles.

The formula used for computing the curvatures is:

$$R_i = K_i R_i$$

Where:
$R_i$ is the radius of corneal surface curvature of $i^{th}$ ring;
$K_i$ is the lumped constant of $i^{th}$ ring; and
$R_i$ is the measured radius of $i^{th}$ ring.
(The lumped constant depends on magnification, ring size, local rate of curvature etc.)

The constants $K_i$ are determined by calibrating the instrument by measuring objects of known radius. These data are stored on a disk, in an EEPROM or some similar means for use by the main program. The provision of a variable focal length camera lens would permit adjustment to compensate the magnification errors which will result from the tolerance of focal length of commercial lenses if desired but the calibration table method is the preferred embodiment.

II. Processing Circuitry and Operation

Figure 1:
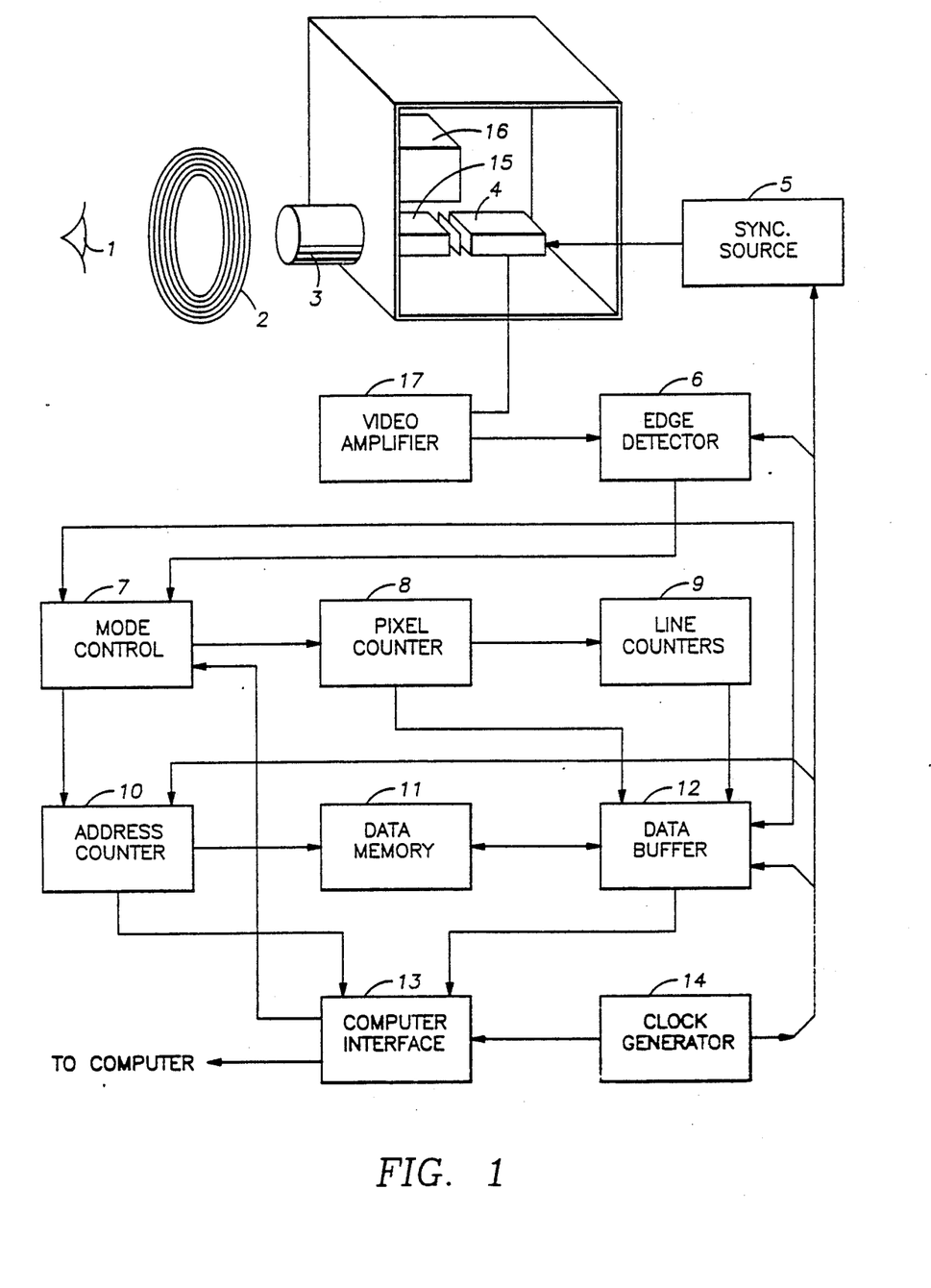
FIG. 1 shows a block diagram of the video components and processing circuitry of the present invention.
Figure 3:
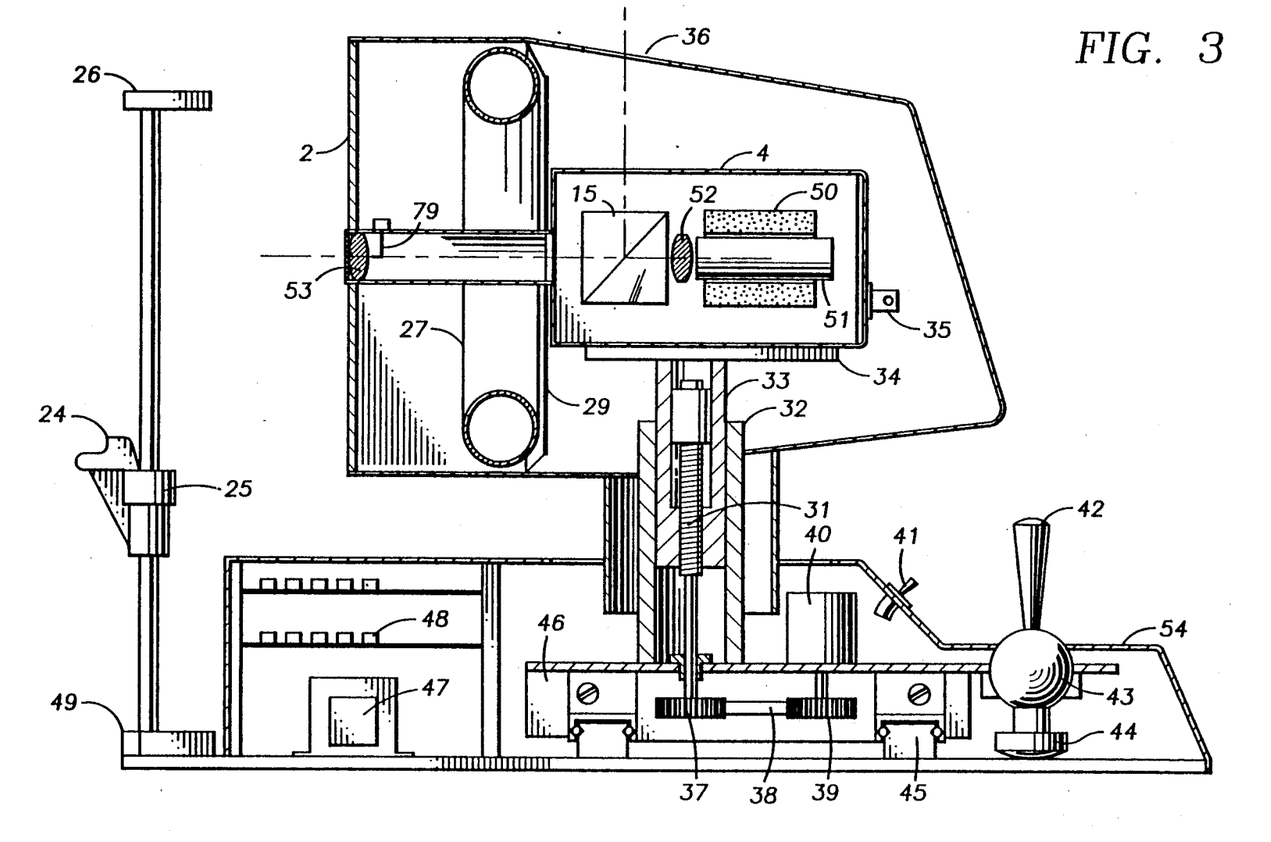
FIG. 3 depicts sectional view of the preferred embodiment of the video keratometer of FIG. 1.

Referring now to FIGS. 1 and 3, the keratometer of the preferred embodiment comprises a placido (2) or similar target, a lens system (3), a television camera (4) for receiving the reflection of the placido (2) from the eye (1), a clock generator running at 14,318,180 Hertz, a sync source (5) providing internal timing, a video amplifier (17) for processing and normalizing the analog signal received from the video camera (4), and an edge detector (6) for locating image brightness discontinuities.

The eye to be examined (1) is positioned according to conventional techniques preferably at a distance of 75 mm from the placido (2) and centered on the optical system. As shown in FIG. 3, an optical fiber (79) preferably is provided at the optical center of the placido (2) and provides a bright point of light for the patient to fixate upon. The placido (2) is in the form of a transilluminated surface of translucent material with the television camera lens (3) centered in the placido (2), and with the lens, in turn, surrounded by concentric circles of opaque material. The placido (2) is illuminated by one or more lamps placed behind the disc surface so the translucent areas are bright circles as viewed by the subject. By this technique an image is provided in a plane anterior to the corneal surface of the eye. The reflection of this image is received by television camera (4) after passing through the lens (3). The lens preferably includes an objective lens located at or near its focal length from the eye, a beam splitter or mirror (15) whereby a portion of the image formed by the objective lens may be diverted to a camera port (36) for photographic recordation of the eye and the placido reflection. A secondary lens (52) receives the remaining image portion is arranged so as to bring the image of the reflection into focus at the photo-sensitive surface of the image tube (51) in the camera (4).

Referring still to FIG. 1, a clock generator (14) preferably comprises a crystal control oscillator operating at 14,318,180 Hertz. The output of clock generator (14) electrically connects to sync source (5), which preferably comprises a conventional television sync generator for synchronizing the television camera (4).

Figure 7:
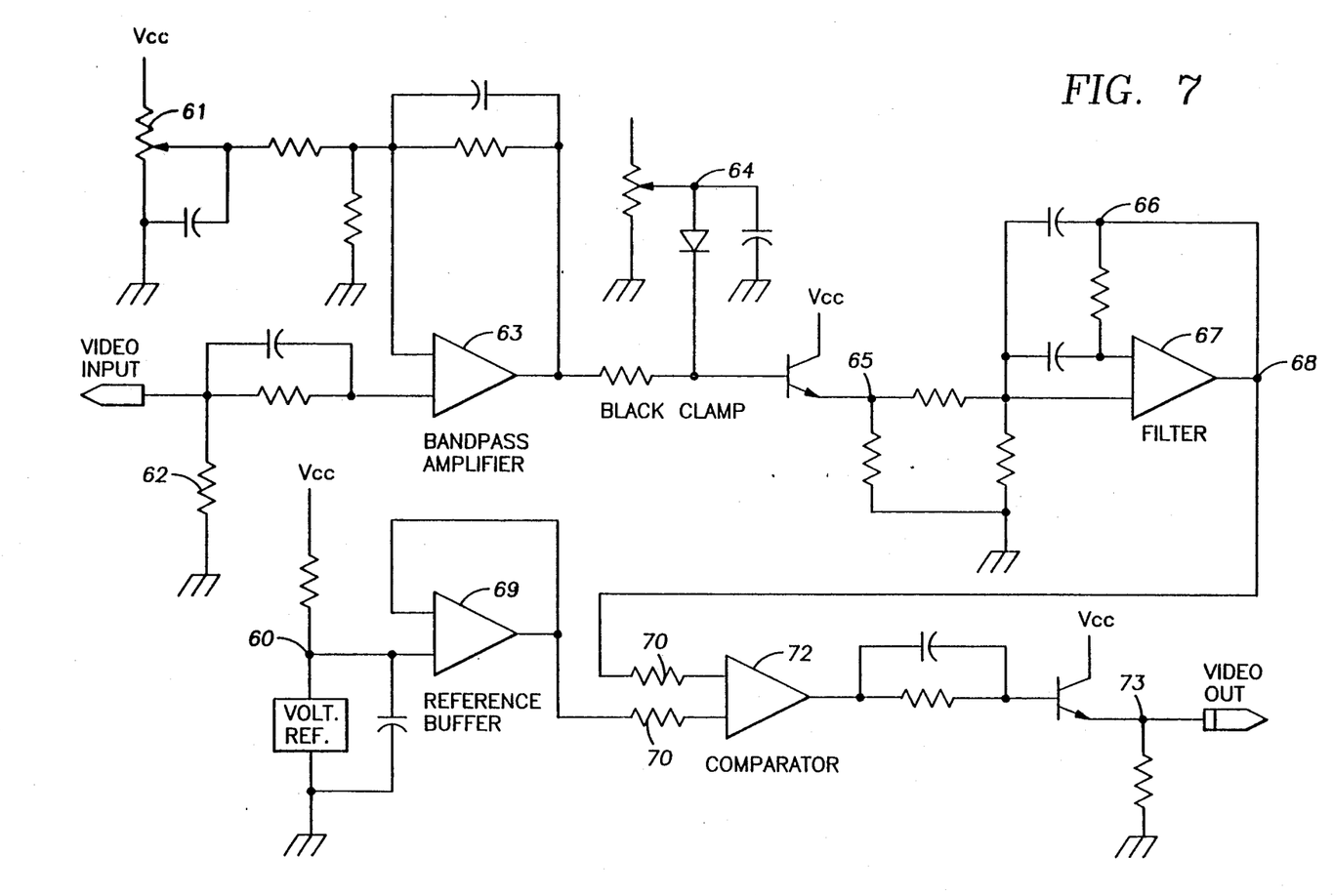
FIG. 7 depicts a schematic diagram of the video amplifier shown in FIG. 1.

The electrical signal from the camera (4) is connected to a video amplifier (17) where the electrical analog of the image of the eye including the reflection of the placido (2) is treated by electronic elements to normalize the signal. Referring now to FIGS. 1 and 7, the incoming video signal from the camera (4) is first treated in a conventional video amplifier (17) which may include a band pass filter of such construction as to pass all of the desired image information but to suppress the noise from the signal as previously described.

Referring still to FIGS. 1 and 7, the video signal from the camera is amplified and impedance matched by a conventional video amplifier (63), which may be provided with D.C. offset compensation means (61) and shading and/or gamma correction circuitry (not shown) which are well known in the art. The signal is D.C. restored in a conventional black-clamp circuit (64) which reestablishes the baseline value. This is followed by an active filter preferably constructed from an operational amplifier (67) and a frequency sensitive feedback network (66). The filter serves to limit the frequency domain of the signal to the region which contains the data. The active filter provides a low impedance output (68) suitable for driving a comparator circuit. The filter preferably is a band pass type wherein the DC component, or baseline value is removed so that the actual comparator switch point can be at or very near the zero crossing point of the signal. This permits the system to be insensitive to changes in illumination level or local reflectance induced level changes which would otherwise shift the comparator switch point in time relative to the signal. Alternatively the data signal is amplified and limited by means such as are employed in FM radio receivers before the comparator stage. Both techniques are designed to have as little hysteresis as possible so that the comparator action is symmetrical for transitions in either direction. A stable voltage reference such as an integrated circuit reference device provides a voltage (60) which is buffered by a conventional voltage follower (69) and impressed on an input terminal of the voltage comparator (72) together with the conditioned video signal via the isolating resistors (70, 71) and the output of the comparator (72) preferably is further amplified and buffered by an emitter follower circuit (73) or other suitable device.

Figure 5:
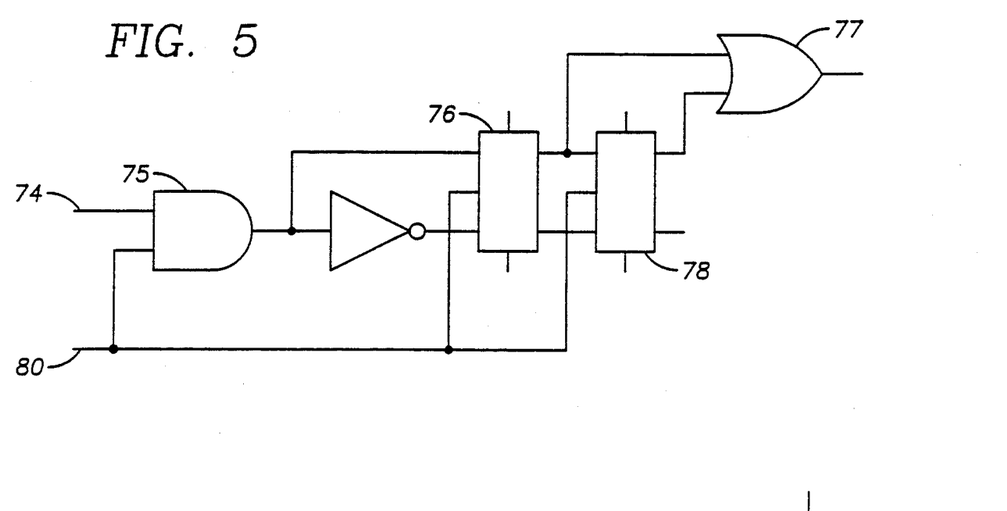
FIG. 5 depicts a schematic diagram of the edge detector shown in FIG. 1.

Referring now to FIGS. 1 and 5, the edge detector (6) receives the output from clock source (14) and video amplifier (17) to convert the signal into a binary form where the ring image edge is true and all other areas of the image are false in binary terms. The buffered comparator output from the video amplifier (17), is used to provide one input (74) to a conventional "and" gate (75) with a second input from the pixel clock oscillator of clock generator (14). When the instantaneous video level exceeds the reference level to the comparator, and when the clock signal is also true, the output of the and gate will provide the inputs to flip-flops (76, 78) which will act as a single bit shift register. The data pulse stream "anded" with the clock signal will be shifted to the right at the rising edge of each clock pulse. Interconnected to the output of the flip-flops (76, 78 is an exclusive-or gate (77). The output of the exclusive-or gate (77) can only be true if the two flip-flops (76, 78) are in a different state which can only occur when the signal from the comparator (74) has been changed on successive clock cycles. A true output from the exclusive-or gate (77) defines a change of brightness level in the incoming video signal after the time domain normalization. This constitutes the data point to be defined in memory and is ultimately used to define the image shape for the computation of the corneal surface shape. The system of interconnections assures the temporal synchronism of the various elements of the present invention. The brightness discontinuities defined in the edge detector (6) constitute the pattern to be analyzed for corneal shape information. When the edge detector (6) locates an image brightness discontinuity it produces a signal in temporal synchronism with the clock signal from the sync source (5).

Referring now to FIG. 5, the edge detector, preferably a delay element connected with an exclusive or gate. In this system the comparator signal which is the electrical analog of the video signal level is gated with the clock signal to generate a serial data stream. The brightness change associated with the edge of a ring reflection will cause a change of state of this data stream from one to zero or conversely. The serial video brightness data in binary form is applied to the and gate (75) and is defined in pixel location form by the second and gate input (80) which is the pixel clock pulse train from the oscillator and which is used to define the image in pixel terms by the and gate (75). A given datum is delayed one clock period by the action of the flip-flops (76 and 78) interconnected as a shift register. The delayed output is compared with the next following data point in an exclusive or gate of conventional construction. It is obvious that the only time the two signals differ is one clock period subsequent to a change of image brightness sufficient to cause a change of comparator output. The output of this comparator is then gated with the pixel clock signal which will result in a series of pulses at clock rate at and only at the time that the ring reflection is encountered. It follows that the condition of the output of the said exclusive or gate will be true only when there has been a change in the state of the input pulse stream. This is when the edge of the image is encountered in time or, in other terms, in position along the raster line.

Referring again to FIG. 1, mode control (7) comprises gating and storage elements to determine the sequence of operations of the several elements of the system. These functions are preferably contained in a "PAL" (Programmable Array Logic) integrated circuit form where the boolean equations for the sequence are implemented. The arrival of the edge signal from edge detector (6) at the mode control (7) causes the numerical content of the pixel counter (8) and the line counter (9) to be transferred by the data buffer (12) into the data memory and also causes the incrementation of the address counter (10) to the next address of memory (11) storage of the determined points which define the image brightness discontinuities.

Referring still to FIG. 1, the pixel counter (8) preferably comprises synchronous binary counter elements so connected as to accumulate a numerical representation of pixel location. The counter (8) is reset by horizontal sync and counts at pixel clock rate so that at any instant the count contained is the location of the beam in the raster in terms of the number of pixels from the left edge of the picture from camera (4).

The line counter (9) construced in accordance with the preferred embodiment is similar to pixel counter (8), except that the clocking signal being counted is the horizontal sync pulse from sync generator (5) and the reset is by vertical sync or alternate field pulse from sync generator (5). The count contained in the line counter (9) is then the location of the raster beam in terms of line number from top to bottom. The combination of the numbers contained in pixel counter (8) and line counter (9) at any instant is the X,Y location of a specific pixel in the picture formed by television camera (4).

Referring still to FIG. 1, the address counter (10) preferably is constructed in similar fashion and the count is incremented by the action of edge detector 6 through the action of the mode control (7) when data is being recorded, or by the computer interface (13) and the mode control (7) when the data is retrieved and passed to the computer for analysis.

After the total area of the picture has been formed by the television camera (4) under control of the sync generator (5) an alternate field signal is generated by the sync generator (5) which terminates the recordation of data that began at the previous alternate field pulse under control of the computer interface (13) and mode control (7). At this time, the computer interface (13) enables the transfer of the data stored in the memory (11) by sequential elements in sequence as determined by the address counter (10), to the associated computer. The computer will sense the not busy-signal generated by the interface (13) and will provide address information to the address counter (10) whereby the content of the memory (11) will be transferred via the data buffer (12) to the computer for analysis. Data buffer (12) comprises three-state buffers which permit the proper interconnection in time of the various data sources on the interconnecting data bus under the control of mode control (7).

A conventional integrated circuit decoder device or devices (not shown) may then be employed to define a narrow band of loci which includes the raster center and from this, generate on the display an alignment or fiducial mark or marks to assist the user in centering the eye for measurement if desired. Similar decoding circuitry may be employed to generate lines to define perpendicular, narrow bands at the image center to facilitate image centering as previously described for the line counter (9). The storage of the numbers contained in the line counter (9) and pixel counters (8) at the time of arrival of a pulse from the edge detector (6) is then the numerical x,y location of each image edge point for later computer analysis. In an alternative embodiment the memory (11) is the memory of the computer and is used by well known DMA (direct memory access) to reduce the system parts count and expedite the speed of the system by concurrent data acquisition and computation. These counts are directed to the memory (11), either internal or shared, by means of the data buffer (12), which are well known in the art.

The resolution of the data stored in this fashion is not a function of the memory size of the host system and thus permits the definition of the image to a much higher resolution limit than would be practical with direct digitization of the image by a "frame grabber" image digitizer and conventional image analysis algorithms used in the prior art. A signal from the associated computer, after the data are stored, initiates the transfer of the memory contents via the interface under control of the mode control (7) and the address counter (10). The overflow of the address counter resets the system. The construction and operation of these elements are well known in the art and commonly understood. As will be evident to one skilled in the art, the computer interface (13) may be by means of serial data loop, parallel bus, and even shared memory in the computer if desired, to increase system speed.

A beam splitter or mirror (15) may be included to permit a camera (16) to be used in conjunction with the electronic system to provide a permanent film image of the eye being measured if desired.

Figure 2:
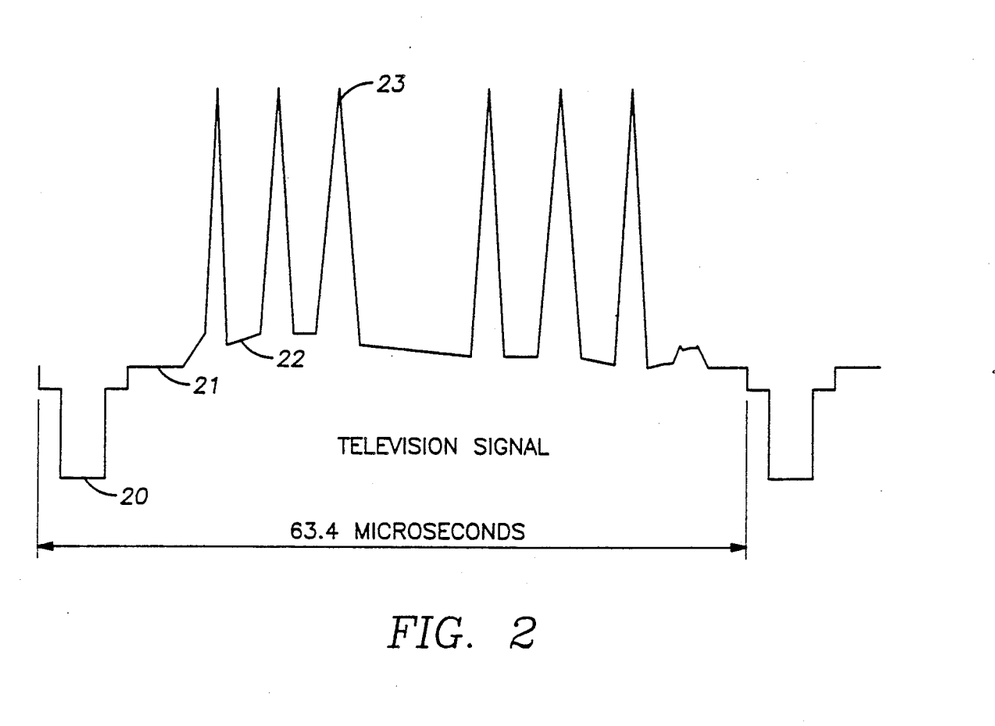
FIG. 2 illustrates a television signal waveform for the television camera of FIG. 1.
Figure 8:
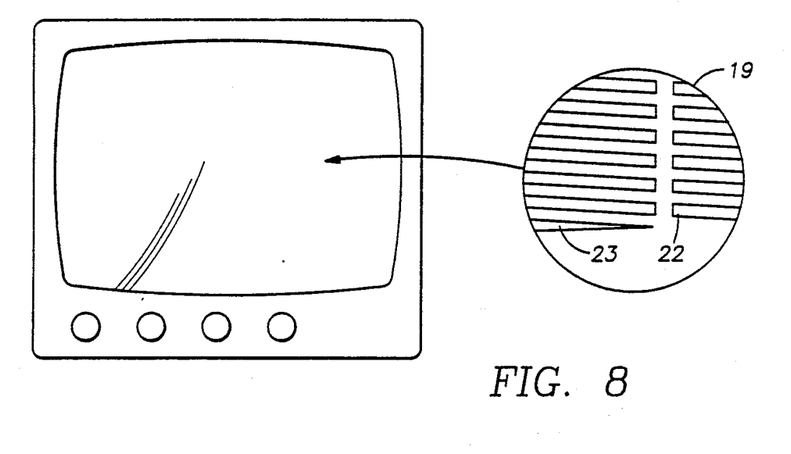
FIG. 8 illustrates the raster display.

FIGS. 2 and 8 illustrate the video signal and time/amplitude relationships. The raster (19) is drawn in successive time intervals by the beam motion under yoke control. As the beam is swept across the tube viewing screen, the beam may be turned-on, causing the line to be written (illuminated) (23) or turned-off leaving the area dark (22). The electrical signal for a single horizontal line is shown in FIG. 2. The electrical waveform shown in FIG. 2 is a single line of the raster with alternating black and white areas with the more positive potential at the top in conventional form. The time between the horizontal sync signals (20) in NTSC format is 1/15750 second or 63.4 microseconds. The horizontal rate is 15,750 lines per second and the field and frame rates are 60 and 30 per second, respectively. From this, it follows that the pixel size can be defined in either size or time domain. The horizontal sync pulse (20) is superimposed on a blanking signal (21) of such amplitude as to insure that the beam in the display is fully off during the retrace interval. The blanking signal is of such level as to assure the beam is turned off while the beam is retraced or repositioned for the subsequent line, at the left edge as viewed. The video signal (22) is depicted at black level, is alternating with six white areas (23). The definition of black and white are in terms of relative voltage magnitude above the "porch" or blanking level. The term porch comes from the waveform of the blanking and sync pulse composite. The "back-porch" or portion of the blanking pulse following the sync pulse is used to contain the phase reference burst signal in composite color transmission, this signal may be present in some embodiments of the present invention but the reference burst signal is not illustrated for clarity.

Referring now to FIG. 3, centered in the surface of the placido (2) opposite the eye is an objective lens (53) which is used in conjunction with a camera lens (52) to image the eye and, consequently, the placido reflection upon the tube (51) of a conventional television camera (4). Given, for example, a focal length of the objective lens of 75 mm, an erect image at optical infinity will be formed by this lens at a lens to subject distance of 75 mm. The television camera lens, (52) forms the image of the reflection of the placido on the cornea as a real image in the plane of the television pickup tube photosensitive surface (51). The television camera (4) will provide an electronic analog of the image which is bandpass filtered and amplitude normalized in conventional amplifier means such as that shown in FIG. 7 and described supra.

The construction of the instrument shown in FIG. 3 is a representative illustration of the means for obtaining the video signals previously described. The subject is placed in front of the instrument with the chin supported in a rest (24) which may be adjusted for subject size in terms of chin to eye dimension. This adjustment (25) is typically a screw operated device. The optical assembly (58) is mounted in suitable "slides" (45, 46) which permit motion in two perpendicular planes without rotation so that either eye may be aligned on the optical axis and the image brought into critical focus by the motions. The placido (2) is illuminated from behind by a lamp (27) which may be a circular fluorescent tube or other type as desired. The assembly is also moveable in the vertical axis by means of a slide (32, 33) under control of a screw (31). The rotation of the screw may be by a knob or a motor drive comprising a motor (40), pulleys (37, 39) and a cooperating belt (38) or other suitable means to permit the elevation of the optical axis to be under operator control for alignment of the optical axis of the instrument with the eye to be measured. The action of a "joy-stick" (42) mounted in a ball and socket system (43) under operator control via a cam or friction member (44) preferably propels the instrument on the slides (45, 46) to facilitate the positioning and focus steps. A brow rest (26) may be mounted on the head support system (49) to insure the fixed position of the eye to the instrument while the adjustment and measurement are made. The patient is requested to focus his eye on the fixation target (79) to assure the coincidence of the optical axes of the instrument with the eye (1). After the positioning and focus step, the operator presses the switch (41) or a foot operated switch, at which time the portions of the image relating to the measurement to be made are captured by the electronic assembly (48) and suitable power supply (47) operatively associated therewith.

Figure 6:
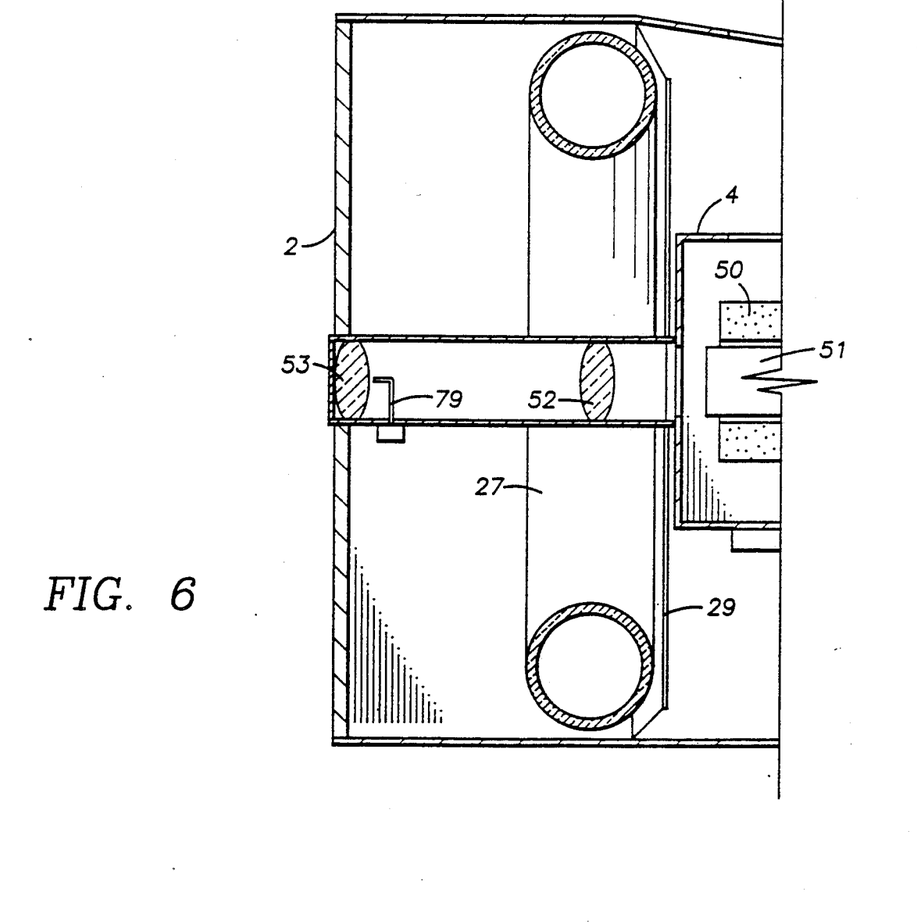
FIG. 6 shows a partial sectional view of an alternative embodiment of FIG. 3.

Referring now to FIG. 6, a partial sectional view of an alternative embodiment of the instrument is shown. The image of the eye is formed at optical infinity by the objective lens (53) and the camera lens (52) projects this image onto the camera faceplate. The light from the lamp (27) is transmitted through the translucent portions of the placido (2) and the reflection of the rings comprising the placido are then imaged upon the television pickup tube (51).

An object (the placido) is reflected from the surface of the cornea and the size of the reflection is measured. The focal length of a convex mirror is one-half of the radius of curvature and the image and object sizes can be related to the focal length. The object in this case is preferably a placido or Placido's disc.

Figure 11:
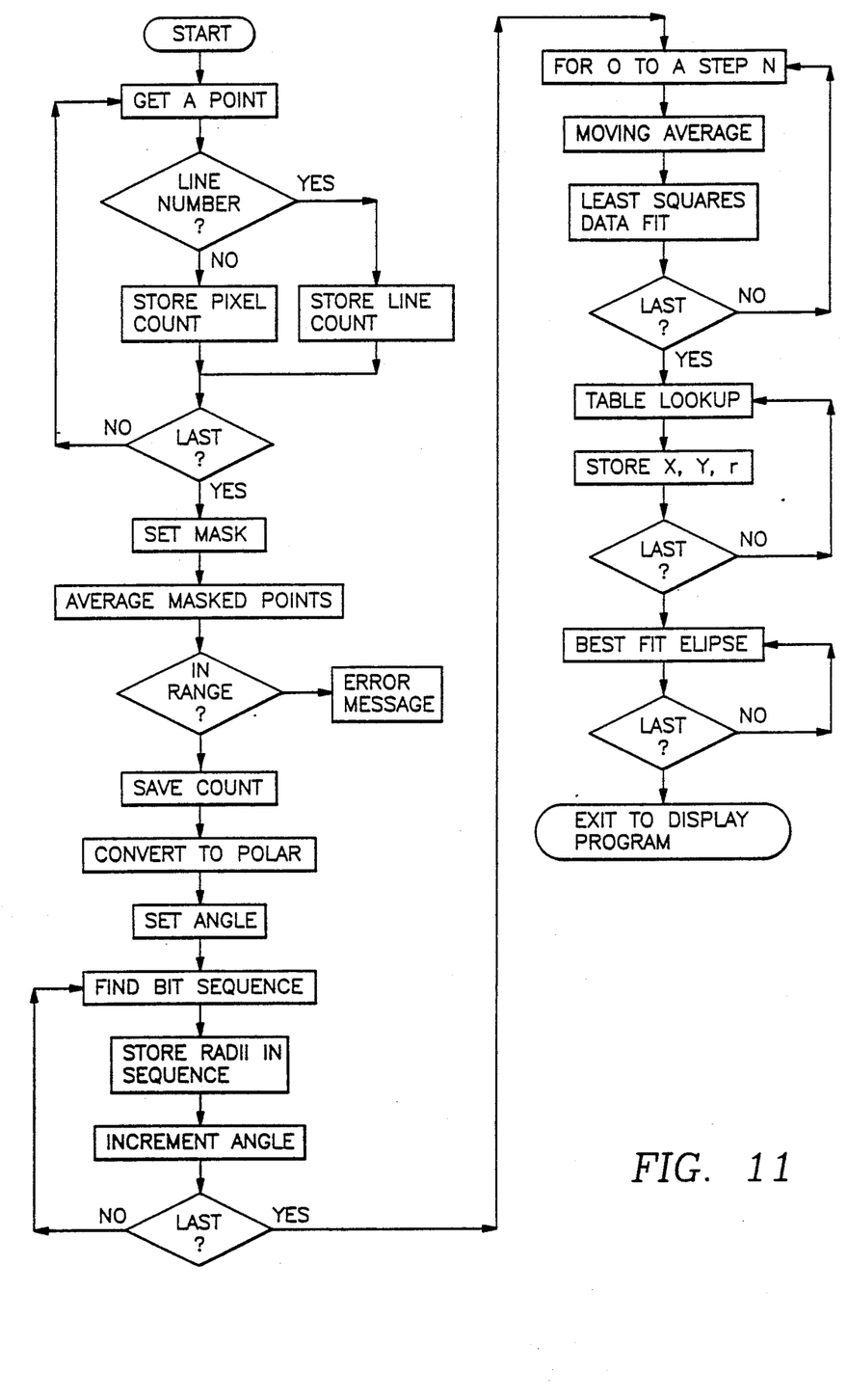
FIG. 11 depicts a flow chart of the operation of the present invention.

Referring now to FIG. 11, the data points which are recorded in memory comprise line and pixel numbers which denote the locus in X, Y terms of each brightness transition in the picture which are over threshold magnitude. These points are cotaminated to some extent by random noise and so must be treated to remove the noise, establish centering and focus accuracy and general quality prior to being converted into final form for use in standard display algorithms for use. As the data points are stored in memory at the time of recordation, the points which define line numbers have been identified by addition of a flag bit in the position commonly occupied by the sign bit. This is possible because the data points all bear a common positive sign and makes sorting simpler by making use of a sign compare instruction available in all computers. The line numbers are stored as a paired table with the data points provided by the pixel numbers in the measurement and the process continues until all data points are so sorted. The end of data in storage is indicated by either a line number or a pixel number being equal to zero which is caused by clearing the entire data memory to zeros prior to each measurement. This technique reduces the number of data points to be treated in the ensuing calculations. A numerical mask is set into the software to define a small area at the center of the picture which defined the location in which the fixation target reflection will be found if the instrument is properly aligned with the eye (1). The reflection of the fixation target must be inside this mask for best accuracy. The data points within a slightly larger area are averaged to define the optical center of the data to be treated. If the averaged data point is within the mask area it is stored as the center point for polar data form conversion, if outside the mask the measurement is aborted. The operator may be notified of the error or an automatic repeat measurement for some given number of tries, commonly 3 can be done prior to the notification as desired. After the data format conversion from cartesian to polar form the angle count is set to zero and the points in radial sequence are stored in a table. This is repeated for as many angles as are desired. The increase in the number of angles enhances later display use but increases the calculation time so the number of angles is user selected. After all desired angles have been converted the data points are examined by distance from center as groups. It should be noted that this is in sequence terms as opposed to discrete distance terms in that the reflection will be closed, nested curves, but not circles or other regular figures in most cases. The radially selected groups are subjected to a smoothing process such as a least squares, moving average to define the shape of the reflection of the placido. To provide the common form of K1, K2, Cylinder and Axis, the innermost smooth curve may be presumed to be an ellipse and the calculations produce the "best fit" ellipse from the smoothed data. From this the K1 and K2 are determined by lookup and interpolation from the calibration data table and the numerical difference becomes Cylinder. The Axis is, of course, the major axis angle of the determined ellipse in anti-clockwise form from 0 degrees in the horizontal plane extending to the right of the origin. The remaining steps take each set of points for successive concentric reflections and smooth them in like fashion. Any data point which fails to fit the smooth curve by more than 2 standard deviations is then deleted and the data resmoothed. The smoothed data are then converted to X, Y, and radius of surface curvature form by table lookup for use in any desired display format.

While a preferred embodiment of the present invention has been described herein, it will be understood that a person skilled in the art may make minor alterations or substitute circuitry and apparatus other than that described without departing from the spirit of the invention.

What is claimed is:

1. A video keratometer for ascertaining the shape of the corneal surface of the eye, comprising:
    imaging means for providing an image on the corneal surface of the eye;
    video means for receiving a reflection of the image from the corneal surface and for transmitting a video signal representative of the reflected image;
    an edge detector for detecting brightness discontinuities in the video signal received from said video means representing edge of the image;

means for defining data points based upon the brightness discontinuities detected by said edge detector;

means responsive to said defining means for determining corneal radius;

means for centering said imaging means for the eye;

locating means responsive to said data points for locating the optical center of said data points;

means for setting a mask, wherein said mask defines preferred data points in the central area of the eye;

means for comparing said preferred data points with said optical center; and display means responsive to said comparing means for displaying an error signal when said optical center lies outside said preferred data points.

2. A video keratometer according to claim 1, wherein said defining means comprises a plurality of counters.

3. A video keratometer according to claim 1, wherein said imaging means comprises a placido's disc.

4. A video keratometer according to claim 1, whererin said edge detector, includes a first and a second flip-flop.

5. A video keratometer according to claim 1, further comprising a synchronous source connected to said video means and said edge detector for synchronizing said video means and said edge detector.

6. A video keratometer according to claim 1, further comprising amplifier means connected between said video means and said detecting means.

7. A video keratometer for mapping the corneal surface of the eye, comprising:

an image upon which the eye fixates;

lens means for forming a reflector of the image from the eye;

means for recording the image formed by said lens means;

means for detecting brightness discontinuities in the image recorded by said recording means;

means for defining data points based upon the brightness discontinuities detected by said detecting means;

means for centering the image on the eye;

determining means responsive to said recording means for determining when the image is not centered on the eye; and said determining means including means for analyzing said data points to determine if said data points are within a central region of the eye.

8. A keratometer according to claim 7, wherein said centering means comprises an optical fiber positioned in the center of the image.

9. A method of ascertaining the shape of the corneal surface of an eye comprising the steps of:

centering an image on the corneal surface of the eye;

receiving a reflection of the image from the corneal surface;

determining data point from the reflected image to define the shape of the corneal surface;

setting a mask to define a theoretical optical center for the eye;

averaging the data points to calculate the center of the data points;

comparing the theoretical optical center with the calculated center; and generating a signal if the calculated center is outside of the theoretical optical center.

* * * * *